United States Patent [19]

Abramovici et al.

[11] 4,076,762

[45] Feb. 28, 1978

[54] CONTINUOUS PROCESS FOR THE REMOVAL OF OTHER HYDROCARBONS FROM SATURATED ALIPHATIC HYDROCARBONS

[75] Inventors: Miron Abramovici, Somerset; Eric W. Stern, Mountainside, both of N.J.

[73] Assignee: Engelhard Minerals & Chemicals Corporation, Iselin, N.J.

[21] Appl. No.: 792,175

[22] Filed: Apr. 29, 1977

[51] Int. Cl.² .......................... C07C 9/14; C07C 7/00; C10G 27/02
[52] U.S. Cl. ................................ 260/676 R; 208/288
[58] Field of Search ............... 208/284, 283, 288, 295, 208/226; 260/666 P, 676 R

[56] References Cited

U.S. PATENT DOCUMENTS

| | | | |
|---|---|---|---|
| 1,788,204 | 1/1931 | Posth et al. | 208/295 |
| 2,721,166 | 10/1955 | Earhart | 208/288 |
| 3,281,484 | 10/1966 | Van Pool | 260/676 R |
| 3,394,200 | 7/1968 | Sargent | 260/676 R |

*Primary Examiner*—George Crasanakis

[57] ABSTRACT

Non-paraffinic hydrocarbons, such as aromatic hydrocarbons, in a stream of paraffinic hydrocarbons are removed in an operation adaptable for continuous operation by contacting the paraffinic hydrocarbon stream with an oxidation system comprising an aqueous solution of hypochlorite, such as sodium hypochlorite, and a ruthenium species, such as ruthenium dioxide, as the oxidation catalyst. The ruthenium species is oxidized by the hypochlorite to a higher oxidation state with resulting selective oxidation of the non-paraffinic hydrocarbons to water-soluble compounds and/or $CO_2$. A stream of paraffinic hydrocarbons having a substantially reduced content of or substantially free of non-paraffinic hydrocarbons is recoverable and, if desired, a stream of recovered paraffinic hydrocarbons may be recycled for additional contact with the oxidation system. Also, the aqueous phase comprising the oxidation system, after separation from the treated paraffinic hydrocarbons, is recycled to contact additional paraffinic hydrocarbons to be treated and/or, from time to time, a portion is separated and treated to reduce the ruthenium species therein which is then recovered and recycled and to convert the hypochlorite in the aqueous phase to the corresponding chloride and for discharge, thereby avoiding build-up in the operation of conversion products, e.g. water-soluble oxygenation material derivable from the selective oxidation of the non-paraffinic hydrocarbons.

17 Claims, 1 Drawing Figure

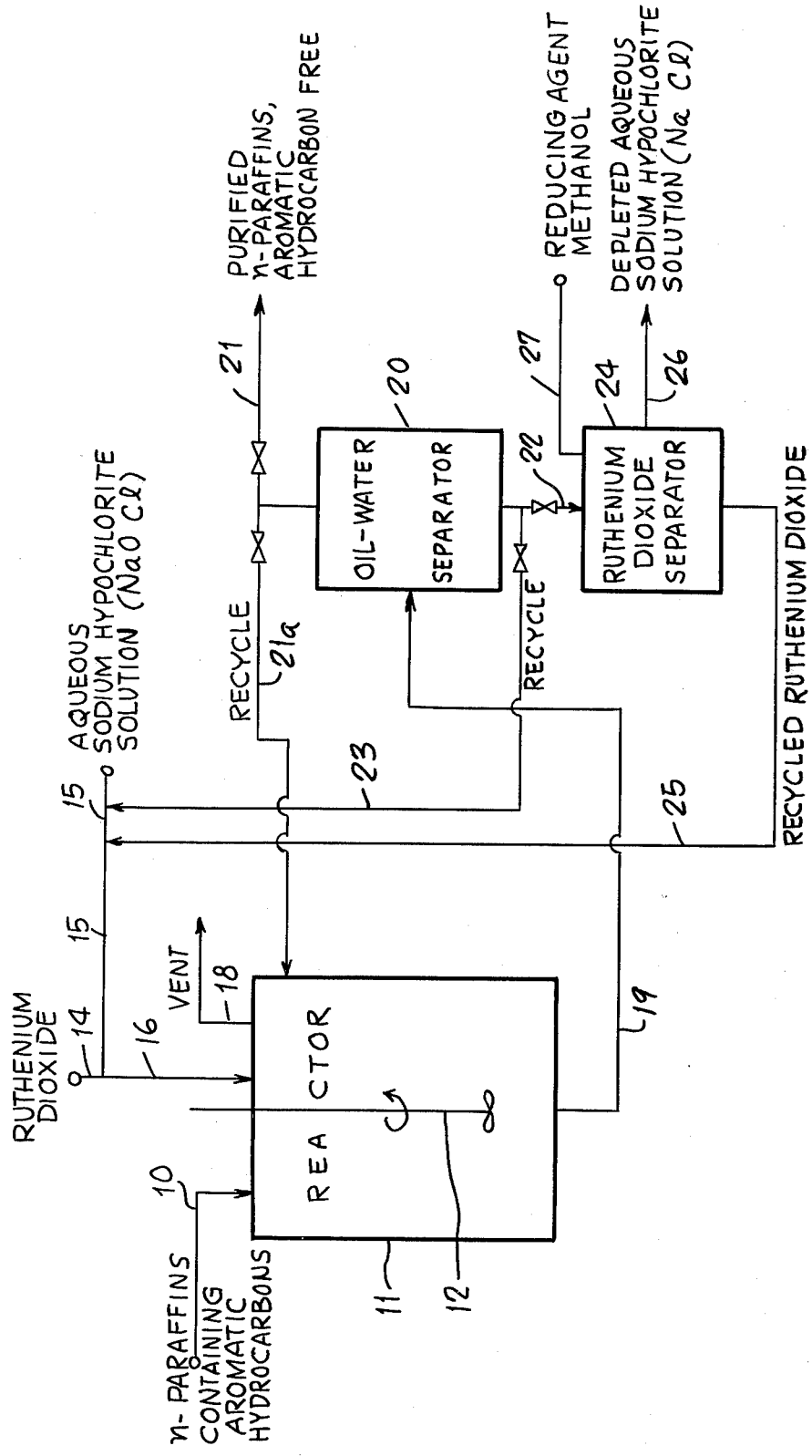

CONTINUOUS PROCESS FOR THE REMOVAL OF OTHER HYDROCARBONS FROM SATURATED ALIPHATIC HYDROCARBONS

This invention relates in a special embodiment to a continuous operation for the selective oxidation of non-paraffinic hydrocarbons in the presence of paraffinic hydrocarbons. More particularly, in accordance with this special embodiment, this invention relates to a continuous process for the selective oxidation of aromatic compounds, particularly aromatic hydrocarbons including aliphatic-substituted aromatic hydrocarbons, e.g. alkyl-substituted aromatic hydrocarbons, and polycyclic aromatic hydrocarbons, in the presence of saturated or paraffinic aliphatic hydrocarbons.

This application is related to copending, coassigned patent application Ser. No. 792,176 filed Apr. 29, 1977 wherein there is described an operation for the removal of non-paraffinic hydrocarbons from a stream of paraffinic hydrocarbons employing an oxidation system comprising an aqueous solution of hypochlorite and a ruthenium species comparable to the oxidation system employed in the practices of this invention. The disclosures of the above-identified application are herein incorporated and made part of this application. The invention described in the above-referred patent application differs from the invention described in this application in that the invention disclosed and claimed in the above-referred patent application is directed to the employment of an aqueous oxidation system comprising an aqueous solution of hypochlorite and a ruthenium species, such as ruthenium dioxide, for the selective oxidation of non-paraffinic hydrocarbons in the presence of paraffinic hydrocarbons. The subject invention disclosed and claimed herein is directed to a special, distinct embodiment of the invention broadly disclosed and claimed in the above-referred patent application. More specifically, the invention disclosed and claimed herein is directed to a substantially continuous process employing an oxidation system comprising an aqueous solution of hypochlorite and a ruthenium species, such as ruthenium dioxide, for the selective oxidation of non-paraffinic hydrocarbons in the presence of paraffinic hydrocarbons, with the removal of the treated paraffinic hydrocarbons and draw-off, from time to time, of the oxidation reaction products resulting from the selective oxidation of the non-paraffinic hydrocarbons to avoid build-up in the aqueous oxidation system of the overall process, when continuously operated, of an undesirable amount of these conversion products.

It is known that ruthenium tetroxide is a powerful oxidizing agent, see U.S. Pat. Nos. 3,409,649 (1968) and 3,479,403 (1969), also J.O.C. 33, 1959 (1968), the article by J. A. Caputo et al entitled "Synthesis and Ionization Constants of meta- and para-substituted cis-3-Phenylcyclobutanecarboxylic Acids" and Tetrahedron Letters 47, 4729 (1967), the article by J. A. Caputo et al, entitled "The Oxidation of Cyclobutanols and Aromatic Rings with Ruthenium Tetroxide".

It is known that saturated aliphatic or paraffinic hydrocarbons, particularly n-paraffinic hydrocarbons, such as liquid n-paraffinic hydrocarbons having a carbon content up to $C_{23}$, such as in the range $C_7$–$C_{18}$, are useful as substrates or feedstock for the production of a single cell protein (SCP) involving the growth of selective microorganisms on such substrates, see Hydrocarbon Processing, pages 104–108, March 1969.

In the utilization of paraffinic hydrocarbons as a substrate for the growth of microorganisms for the production of SCP, it is desirable that the paraffinic hydrocarbons so employed be substantially free of non-paraffinic hydrocarbons, particularly with respect to being substantially free of aromatic compounds, such as aromatic hydrocarbons, or have an aromatic compound or non-paraffinic hydrocarbon content such that the growth of the microorganisms is not inhibited and/or the SCP material produced is readily harvested and is free of any undesirable materials, such as aromatic compounds.

It is an object of this invention to provide a continuous method for the selective oxidation of one hydrocarbon type in the presence of another hydrocarbon type.

It is another object of this invention to provide a substantially continuous method for the separation of non-aliphatic and/or non-saturated hydrocarbons, particularly aromatic hydrocarbons, from saturated aliphatic hydrocarbons.

How these and other objects of this invention are achieved will become apparent in the light of the accompanying disclosure and with reference to the accompanying drawing wherein is illustrated a process flow scheme in accordance with this invention for the removal of aromatic hydrocarbons from an n-paraffinic hydrocarbon stream.

In accordance with this invention, it has been discovered that a high oxidation state ruthenium species, i.e. higher than ruthenium dioxide, is useful in a substantially continuous operation as an oxidizing agent for the selective oxidation of non-aliphatic and/or non-saturated hydrocarbons, particularly aromatic compounds, such as aromatic hydrocarbons, in the presence of saturated aliphatic hydrocarbons, such as n-paraffins. The aromatic compounds, e.g. aromatic hydrocarbons which may be present as an undesirable component in an aliphatic paraffinic hydrocarbon stream, such as an n-paraffinic hydrocarbon-containing stream, are removed during and/or after oxidation.

More specifically, in accordance with the practices of this invention a stream, such as a hydrocarbon stream containing saturated aliphatic hydrocarbons together with non-saturated and/or non-aliphatic compounds, e.g. hydrocarbons, particularly aromatic compounds, such as aromatic hydrocarbons, is contacted with a mixture comprising a low oxidation state ruthenium species, e.g. ruthenium dioxide, and an aqueous hypochlorite solution, such as an aqueous sodium hypochlorite solution. The ruthenium species, e.g. ruthenium dioxide, in the presence of the aqueous hypochlorite solution is converted to a higher oxidation state ruthenium species. In turn, the higher oxidation state ruthenium species selectively oxidizes those compounds other than the saturated aliphatic hydrocarbons, such as the aromatic compounds and aromatic hydrocarbons, with the resulting conversion of the aromatic compounds and aromatic hydrocarbons to compounds which are readily removable, such as carbon dioxide and/or water-soluble oxygenated derivatives. More than one higher oxidation state ruthenium species, such as ruthenates, perruthenates and mixtures thereof, may be present or employed in the practices of this invention.

In the above-described treatment, aliphatic paraffinic hydrocarbons, particularly the n-paraffins, are refractory and tend not to be oxidized, with the result that the non-aliphatic and/or non-saturated compounds, e.g. aromatic hydrocarbons, present along with the saturated aliphatic or paraffinic hydrocarbons are selectively oxidized to readily removable compounds. In the above-described operation involving substantially continuous selective oxidation of the non-aliphatic and/or non-saturated compounds in the presence of the paraffinic hydrocarbons, the high oxidation state ruthenium species which is derived from the admixture of a low oxidation state ruthenium species, such as $RuO_2$, and aqueous hypochlorite solution, is reconverted to the corresponding low oxidation state ruthenium species, such as $RuO_2$, which, in turn, is reconverted or reoxidized in the presence of the aqueous hypochlorite solution to additional higher oxidation state ruthenium species which is again utilized as the active oxidizing agent for the selective oxidation of the above-mentioned compounds in the presence of the paraffinic hydrocarbons. Accordingly, only a small or catalytic amount of the low oxidation state ruthenium species, such as $RuO_2$, need be present along with the aqueous hypochlorite solution in the practices of this invention. As indicated, the ruthenium dioxide is present in small, catalytically effective amounts; however, the aqueous hypochlorite solution is employed in at least a substantially stoichiometric amount relative to the compounds, e.g. aromatic hydrocarbons, undergoing oxidation; usually desirably the hypochlorite is present or utilized in stoichiometric excess.

The overall chemical reaction sequence in accordance with the practices of this invention may be exemplified as set forth hereinbelow:

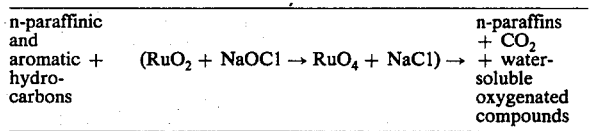

After contacting of the hydrocarbons with the aqueous, higher oxidation state ruthenium oxidation system, the reaction mixture is withdrawn, preferably substantially continuously, from the reactor to an oil-water separator wherein the resulting treated paraffinic hydrocarbons are recovered as product, at least in part, if the desired purity is obtained; if not, the resulting treated aliphatic paraffinic hydrocarbons are recycled for additional contact and treatment. The water phase from the oil-water separator comprising the aqueous oxidation system made up of a hypochlorite and a higher oxidation state ruthenium species is withdrawn from the separator and desirably at least a portion is recycled to the reactor. From time to time, at least a portion of the aqueous oxidation phase is removed and treated with a reducing agent to reduce the higher oxidation state ruthenium species therein to its lower state, such as to ruthenium dioxide, which is then separated, such as by filtration, and recycled to the reactor, the remaining aqueous phase, such as the filtrate, now containing the corresponding chloride derived from the hypochlorite and water-soluble oxygenated compounds dissolved and/or suspended therein is recovered and withdrawn from the system in order to prevent the build-up of an undesirable amount of oxidation products in the aqueous oxidation medium.

Aromatic compounds and hydrocarbons which are selectively oxidized in accordance with this invention in the presence of saturated aliphatic hydrocarbons include the substituted monocyclic aromatic compounds and hydrocarbons, such as the aliphatic-substituted benzenes, e.g. alkyl-substituted benzenes, the alkenyl-substituted benzenes, the polycyclic aromatic compounds and hydrocarbons including the fused polycyclic or polynuclear aromatic compounds and hydrocarbons and derivatives, e.g. naphthalene, anthracene and phenanthrene, and the unfused polynuclear aromatic compounds, such as the biphenyls, and the corresponding aliphatic hydrocarbon-substituted polycyclic or polynuclear aromatic hydrocarbons. Of special interest would be those aromatic compounds and hydrocarbons which have a boiling point in the boiling point range of aliphatic paraffinic hydrocarbons having a carbon atom content in the range of about $C_6$ to about $C_{23}$, more or less. Of special interest would be those aromatic hydrocarbons which have a boiling point in the boiling point range of the $C_7$-$C_{18}$ normal paraffinic hydrocarbons.

The saturated or paraffinic aliphatic hydrocarbons, which are refractory to oxidation in the practices of this invention include, as indicated hereinabove, the aliphatic paraffinic hydrocarbons, particularly the n-paraffinic hydrocarbons or n-alkanes. Saturated aliphatic hydrocarbons having a carbon content in the range from about $C_6$ up to about $C_{23}$ containing in admixture therewith minor amounts of other non-saturated, and/or non-aliphatic hydrocarbons which may also possess the same above-mentioned carbon content, e.g. aromatic hydrocarbons, usually below about 10% by weight, e.g. in the range 0.001 to about 2-5% by weight, are usefully treated in accordance with the practices of this invention.

The saturated aliphatic hydrocarbons useful for the treatment in accordance with the practices of this invention include the normally liquid saturated aliphatic hydrocarbons, particularly the normally liquid n-paraffinic or straight chain paraffinic hydrocarbons, i.e. such hydrocarbons having a melting point up to about 100° C., more or less, such as a melting point in the range about −100° to about 75° C.

As indicated hereinabove, in the practices of this invention the oxidation of the non-aliphatic and/or non-saturated compounds, such as aromatic hydrocarbons, in the presence of saturated aliphatic hydrocarbons, such as the n-paraffinic hydrocarbons, is carried out by employing as the oxidizing agent a mixture of one or more ruthenium species or compound of a relatively low oxidation state, such as ruthenium dioxide, and an aqueous hypochlorite solution. The aqueous hypochlorite solution, as also indicated hereinabove, may comprise an aqueous alkali metal hypochlorite solution, such as aqueous sodium hypochlorite, aqueous potassium hypochlorite or mixtures thereof, or may comprise an aqueous alkaline earth metal hypochlorite, such as calcium hypochlorite, or mixtures thereof or with an aqueous alkali metal hypochlorite. Mixtures of one or more of the above-described hypochlorites, including hypochlorous acid, are useful in the practices of this invention. It is preferred, however, to employ aqueous sodium hypochlorite, such as an aqueous sodium hypochlorite solution having a concentration in the range of about 0.1 to about 15-20% by weight and at a suitable pH, such as a pH in the range from about 5 to about 11. The above-indicated hypochlorite solution concentration range and pH would encompass suitable aqueous hypochlorite solutions derived from hypochlorites other than sodium hypochlorite and mentioned hereinabove.

The ruthenium species, such as ruthenium dioxide, employed in combination with an aqueous hypochlorite solution is preferably finely divided. Initially, if desired and as indicated hereinabove, instead of ruthenium dioxide other ruthenium species, organic or inorganic, might be employed. Specifically, any organic or inorganic ruthenium salt which has an anion which does not retard the formation of the desired higher oxidation state ruthenium species oxidizing agent in the presence of hypochlorite solution would be useful, such as ruthenium halides, e.g. ruthenium trichloride. The above-identified patents, U.S. Pat. No. 3,409,649 and U.S. Pat. No. 3,479,403, contain a listing of ruthenium compounds, other than ruthenium dioxide, which are useful in the selective oxidation operation in accordance with this invention.

The continuous selective oxidation reaction in accordance with this invention involving contact between the saturated aliphatic (straight chain paraffinic) hydrocarbon stream to be treated and purified and the aqueous hypochlorite solution is conveniently carried out at ambient pressure, although subatmospheric or superatmospheric pressures may be employed during the reaction. The reaction is also conveniently carried out at ambient temperatures, such as a temperature at which the hydrocarbons undergoing treatment are maintained in liquid phase, such as a temperature of about 15°–30° C., more or less. If desired, a lower reaction or contacting temperature, such as a temperature as low as about 10° C. or lower, or a higher reaction or contacting temperature as high as 75° C. or higher might be employed depending upon the makeup of the hydrocarbons undergoing treatment and the makeup of the hypochlorite solution employed in combination with the ruthenium species or compound for effecting the selective oxidation of the non-aliphatic, non-saturated hydrocarbons. The reaction should desirably be carried out under conditions such that intimate contact is effected between the hydrocarbons in the liquid phase with the selective oxidizing system comprising the ruthenium species or compound (ruthenium dioxide) and the hypochlorite. In general, however, any suitable, practical operating temperature may be employed in the practice of this invention.

A suitable technique for effecting continuous reaction between the hydrocarbon stream undergoing treatment and the ruthenium-hypochlorite oxidizing system would involve the substantially simultaneous and/or continuous and/or intermittent addition of the hydrocarbons and the ruthenium-hypochlorite oxidizing system to a reactor while the resulting reaction admixture is vigorously agitated. In this operation, only a small catalytic amount of the ruthenium component of the oxidizing system need be exmployed. The hypochlorite component of the oxidizing system, as indicated hereinabove, can be added continuously or intermittently or substantially all at one time. Since the ruthenium component need only be employed in small catalytic amounts and the higher oxidation state ruthenium active oxidizing agent is regenerated during the reaction in the presence of the sodium hypochlorite or added hypochlorite, the reaction is essentially controlled by the amount of hypochlorite added or present during the reaction. If a stoichiometric amount of hypochlorite, e.g. sodium hypochlorite, is added relative to the compounds or hydrocarbons undergoing oxidation, upon completion of the reaction the added hypochlorite should be converted to the corresponding salt, such as sodium hypochlorite to sodium chloride, and the ruthenium compound employed, such as ruthenium dioxide, would appear as a solid, finely divided ruthenium dioxide. A stoichiometric excess, e.g. about 0.2–5.0 molar excess, of hypochlorite is preferred in the practices of this invention.

The contacting of the hydrocarbon stream with the ruthenium-hypochlorite oxidizing system may be carried out in a concurrent contacting operation or a countercurrent contacting operation, such as in a tower packed with a permeable mass of solid contact material. In general, any suitable means or technique for effecting liquid-liquid and/or liquid solids contact would be suitable for use in the practices of this invention.

Upon completion of the reaction with resulting conversion of the contaminating materials to be removed, such as aromatic hydrocarbons, to innocuous products or products which are readily removed, such as carbon dioxide or water-soluble oxygenated compounds, the resulting reaction admixture would be recovered and segregated and portions thereof recycled as desired. The resulting treated hydrocarbons in the reaction admixture, now comprising substantially only saturated aliphatic hydrocarbons, e.g. n-paraffinic hydrocarbons, are at least in part withdrawn as product after settling or separation from the aqueous phase, such as the aqueous phase containing the aqueous hypochlorite or depleted aqueous hypochlorite, i.e. sodium chloride derived from sodium hypochlorite and the ruthenium species or compound employed, e.g. finely divided solid ruthenium dioxide. If desired, the separated aqueous hypochlorite-containing phase can be recycled to contact additional hydrocarbons. Also, if desired, a portion of the separated aqueous hypochlorite-containing phase can be treated to reduce the hypochlorite therein to the corresponding chloride, with resulting lowering of the oxidation state of the ruthenium species therein. The thus-treated aqueous phase containing aqueous sodium chloride and finely divided ruthenium dioxide is then further treated, such as by filtration, for the removal of the solid ruthenium dioxide which could be returned to the reactor for contact with additional aqueous hypochlorite to react or treat additional hydrocarbons in accordance with the practices of this invention. The remaining segregated or separated aqueous phase, which would contain, for example, sodium chloride and water-soluble oxygenated derivatives of the hydrocarbons undergoing oxidation, could then be discharged and separately treated for the recovery of any values therefrom.

Reference is now made to the drawing which schematically illustrates one embodiment of the practices of this invention directed to the continuous selective oxidation of aromatic hydrocarbons in the presence of n-paraffins.

As illustrated in the drawing, an aromatic hydrocarbon-containing n-paraffin stream from a suitable source, not shown, is supplied via line 10 to reactor 11 wherein it is intimately mixed, exmploying agitator 12, with an admixture of ruthenium dioxide supplied from a suitable source, not shown, via line 14 with aqeuous hypochlorite solution, such as an aqueous sodium hypochlorite solution supplied from a suitable source, not shown, via line 15, the resulting admixture of ruthenium dioxide and aqueous sodium hypochlorite being supplied to reactor 11 via line 16 for reaction with the aromatic hydrocarbons within reactor 11. Desirably, the aqueous hypochlorite solution is supplied to reactor 11 in stoichiometric excess relative to the aromatic hydrocarbons therein. Vent line 18 is provided in the upper portion of reactor 11 to avoid any undue pressure buildup within reactor 11.

There is withdrawn from the bottom of reactor 11 via line 19 a reaction admixture comprising the n-paraffinic hydrocarbons and the aqueous phase comprising the ruthenium oxidation species and the hypochlorite. This reaction admixture is supplied via line 19 to oil-water separator 20 wherein, upon settling, the resulting treated hydrocarbons, desirably now comprising substantially only n-paraffins, substantially free of aromatic hydrocarbons, are removed from the upper portion of separator 20 via line 21. In the continuous treatment embodiment of a hydrocarbon stream in accordance with the practices of this invention, the treated n-paraffins would be withdrawn continuously or intermittently from oil-water separator 20 via line 21. A remaining portion, in any amount desired depending upon the purity desired in the product stream withdrawn via line 21, would be recycled continuously or intermittently to reactor 11 via line 21a. Further, the aqueous phase containing the active oxidizing ruthenium species and hypochlorite would be recovered from the bottom of oil-water separator 20 and recycled continuously or intermittently to reactor 11 via lines 23, 15 and 16 to contact the hydrocarbons within reactor 11.

From time to time, an amount of the aqueous phase containing the active ruthenium oxidizing species along with the sodium hypochlorite would be withdrawn continuously or intermittently from oil-water separator 20 via line 22 and supplied to ruthenium dioxide separator 24 wherein a suitable, preferably organic, reducing agent which is readily oxidized, such as low molecular weight alcohol or aldehyde, e.g. methanol, would be supplied via line 27 to effect conversion of the hypochlorite to chloride and resulting reduction of the active ruthenium oxidizing species to ruthenium dioxide which, if desired, could be separated, e.g. by filtration, and returned to reactor 11 via lines 25, 15 and 16. The remaining aqueous phase or filtrate, now containing sodium chloride together with water-soluble oxygenated organic compounds derived from the materials or hydrocarbons which are oxidized within reactor 11, is removed continuously or intermittently from separator 24 via line 26, thereby avoiding a build-up of these materials in the system.

The above-described embodiment in the practices of this invention directed to a continuous operation would, as indicated, preferably employ a stoichiometric excess of sodium hypochlorite solution relative to the contaminating component, e.g. aromatic hydrocarbons, in the n-paraffinic hydrocarbon stream undergoing treatment or purification within reactor 11. By following this embodiment, continuous process, of the practice of this invention, an n-paraffinic hydrocarbon stream of substantially any desired degree of purity with respect to n-paraffin content is recoverable via line 21.

The following is an example of one embodiment of the practices of this invention for the removal of aromatic hydrocarbons from an n-paraffinic hydrocarbon stream, the n-paraffinic hydrocarbons being comprised of n-paraffins having a carbon atom content (per molecule) in the range from about $C_8$ to about $C_{16}$ and containing a minor amount of aromatic hydrocarbons in the range of about 0.01–0.5 to about 2.5% by weight of the stream. The n-paraffinic hydrocarbon stream at a rate of about 50 barrels (U.S.) per hour is introduced into a reactor where it is mixed vigorously with an aqueous admixture comprising ruthenium dioxide and aqueous sodium hypochlorite. The aqueous sodium hypochlorite is added in an amount or hourly rate to the reactor in stoichiometric excess relative to the aromatic hydrocarbons therein to be oxidized and removed. The added aqueous sodium hypochlorite solution conveniently usefully has a concentration of about 5% by weight sodium hypochlorite and a pH of about 9.5. As indicated, finely divided ruthenium dioxide is initially added in a small amount, about 0.5–10 pounds, more or less, along with the aqueous hypochlorite solution to contact the hydrocarbons within the reactor and additional ruthenium dioxide need not be again added save to make up losses of the initial charge upon continuous operation of the overall system.

The reactants supplied to the reactor and the resulting reaction admixture during the oxidation reaction (selective oxidation of the aromatic hydrocarbons) are usually at about ambient temperature or slightly more or less than ambient temperature, such as in the range of 10°–50° C., more or less, depending upon the amount of aromatic hydrocarbons in the hydrocarbon stream undergoing reaction and the temperature of the reactants supplied to the reactor. Carbon dioxide formed due to oxidation of the aromatic hydrocarbons along with other gases or vapors which might be formed are vented upon the reactor.

The rate of introduction of the reactants and the rate of withdrawal of the resulting reaction mixture are adjusted so as to provide a reactants residence time within the reactor of from about five minutes to about one hour, while carrying out the reaction with vigorous agitation. Upon withdrawal of the resulting reaction mixture from the reactor, the hydrocarbon phase component is separated from the aqueous phase component thereof. The resulting separated hydrocarbon phase now has a substantially reduced aromatic hydrocarbon content. The aqueous phase containing sodium hypochlorite solution and the ruthenium oxidizing species is recycled or treated in accordance with this invention as illustrated in the accompanying drawing.

In this example or embodiment of the practices of this invention, the treatment of the aromatic-containing hydrocarbon stream, which is comprised predominantly of n-paraffinic hydrocarbons, is carried out substantially continuously, i.e. the reactants in the desired amounts are added at substantially the same time to the reactor. Obviously, many variations of the above and other techniques for bringing the reactants together for effecting the oxidation of the undesirable contaminating components and for carrying out the above-described operations substantially continuously are suitable in the practices of this invention. In the practices of this invention, as indicated hereinabove, it is desirable to add only sufficient excess aqueous hypochlorite solution to generate the powerful active high oxidation state ruthenium species oxidizing agent, e.g. ruthenium tetroxide, and to replenish the same to maintain the desired stoichiometric excess until the contaminants in the n-paraffinic hydrocarbon stream undergoing treatment have been removed by oxidation or converted to readily removable compounds, such as water-soluble oxygenated compounds.

Although in the practices of this invention ruthenium dioxide is the preferred low oxidation state ruthenium compound or species employed in association with the aqueous hypochlorite solution, e.g. aqueous sodium hypochlorite, for the production of a relatively high oxidation state ruthenium compound or species, as indicated hereinabove other ruthenium compounds or species are also usefully employed in association with the aqueous hypochlorite solution for the production of the higher oxidation state ruthenium species. Other suitable ruthenium compounds include the ruthenium halides, e.g. ruthenium trichloride and other inorganic ruthenium salts, as well as the ruthenium salts of fatty acids, such as the $C_2$ and higher fatty acids, ruthenium acetate, ruthenium propionate and ruthenium butyrate. For a larger listing of suitable ruthenium compounds including ruthenium-containing chelates useful in the practices of this invention, see U.S. Pat. No. 3,409,649 mentioned hereinabove.

Although emphasis has been placed on the selective oxidation of aromatic hydrocarbons in the presence of saturated aliphatic hydrocarbons in the practices of this invention, compounds other than aromatic hydrocarbons or, more particularly, organic compounds other than saturated aliphatic hydrocarbons, are also suitably removed by the selective oxidation in accordance with the practices of this invention. For example, compounds other than saturated aliphatic hydrocarbons which would appear to be selectively oxidized in accordance with the practices of this invention in the presence of saturated aliphatic hydrocarbons, particularly n-paraffinic hydrocarbons, include aromatic compounds, substituted aromatic hydrocarbons, unsaturated aliphatic compounds, including unsaturated aliphatic hydrocarbons, cycloaliphatic compounds, including cycloaliphatic hydrocarbons, saturated for unsaturated. In general, the practices of this invention are particularly applicable for the removal by selective oxidation of contaminating compounds in the presence of saturated aliphatic compounds, particularly n-paraffinic hydrocarbons.

As will be apparent to those skilled in the art in the light of the foregoing disclosure, many modifications, alterations and substitutions are possible in the practice of this invention without departing from the spirit or scope thereof.

We claim:

1. A method for treating saturated aliphatic hydrocarbons containing in admixture therewith compounds selected from the group consisting of aromatic hydrocarbons, substituted aromatic hydrocarbons, unsaturated aliphatic hydrocarbons, saturated cycloaliphatic hydrocarbons and unsaturated cycloaliphatic hydrocarbons for the removal of said compounds which comprises (a) contacting said admixture with a selective oxidizing aqueous hypochlorite solution containing a low oxidation state ruthenium compound convertible in the presence of said hypochlorite to a higher oxidation state ruthenium compound capable of selectively oxidizing said compounds, said aqueous hypochlorite being present in a stoichiometric excess relative to said compounds in said admixture, said contacting resulting in the selective oxidation of said compounds to carbon dioxide and/or water-soluble oxygenated compounds, (b) recovering the resulting hydrocarbon reaction phase from the aqueous phase, (c) withdrawing from said recovered hydrocarbon phase at least a portion of said saturated aliphatic hydrocarbons as product, (d) returning at least a portion of the aqueous phase from step (b) to said contacting step (a), (e) intermittently withdrawing a portion of said aqueous phase separated from step (b), (f) adding to said intermittently withdrawn portion of said aqueous phase a reducing agent for the conversion of hypochlorite in said aqueous phase to corresponding chloride and for the reduction of the higher oxidation state ruthenium compound to said low oxidation state ruthenium compound, (g) recycling said low oxidation state ruthenium compound from step (f) to said contacting step (a), and (h) withdrawing from step (f) said resulting aqueous phase containing said corresponding chloride and said water-soluble oxygenated organic compounds derived from the selective oxidation of said compounds.

2. A method in accordance with claim 1 wherein said hypochlorite is sodium hypochlorite.

3. A method in accordance with claim 1 wherein said low oxidation state ruthenium compound is ruthenium dioxide.

4. A method in accordance with claim 1 wherein said low oxidation state ruthenium compound is a ruthenium halide.

5. A method in accordance with claim 4 wherein said ruthenium halide is ruthenium trichloride.

6. A method in accordance with claim 1 wherein said saturated aliphatic hydrocarbons are $C_6$–$C_{23}$ n-paraffinic hydrocarbons.

7. A method in accordance with claim 1 wherein said saturated aliphatic hydrocarbons are n-paraffinic hydrocarbons and wherein said compounds are aromatic hydrocarbons.

8. A method in accordance with claim 1 wherein said hypochlorite is present in a 0.2–5.0 molar excess relative to said compounds.

9. A method in accordance with claim 1 wherein said hypochlorite is provided by an aqueous sodium hypochlorite solution containing sodium hypochlorite in an amount in the range from about 0.01 –0.1% to about 15% by weight.

10. A method in accordance with claim 1 wherein said aqueous hypochlorite solution has a pH in the range from about 5 to about 11.

11. A method in accordance with claim 1 wherein the contacting of said admixture with said selective oxidizing hypochlorite solution is carried out at a temperature in the range from about 10° C. to about 75° C.

12. A method in accordance with claim 1 wherein said compounds are present in said admixture with said saturated aliphatic hydrocarbons in the range from about 0.00001–0.0001% to about .2% by weight based on said admixture.

13. A method in accordance with claim 1 wherein said compounds are present in admixture with said saturated aliphatic hydrocarbons in a minor amount up to about 10% by weight based on said admixture.

14. A method in accordance with claim 1 wherein said contacting of said admixture with said selective oxidizing solution is carried out in a continuous concurrent contacting operation.

15. A method in accordance with claim 1 wherein said contacting of said admixture with said selective oxidizing solution is carried out in a continuous countercurrent contacting operation.

16. A method in accordance with claim 1 wherein the contacting of said admixture with said selective oxidizing solution is carried out over a period of time in the range from about 5 minutes to about 1 hour.

17. A method in accordance with claim 1 wherein said saturated aliphatic hydrocarbons comprise n-paraffinic hydrocarbons having a carbon atom content in the range $C_6$–$C_{22}$ and wherein said compounds have a boiling point range in the boiling point range of said saturated aliphatic hydrocarbons making up said admixture.

* * * * *

UNITED STATES PATENT OFFICE
CERTIFICATE OF CORRECTION

Patent No. 4,076,762          Dated February 28, 1978

Inventor(s) Miron Abramovici et al.

It is certified that error appears in the above-identified patent and that said Letters Patent are hereby corrected as shown below:

Column 9, line 31, "for" should read -- or --.

Signed and Sealed this

Seventh Day of November 1978

[SEAL]

Attest:

RUTH C. MASON
*Attesting Officer*

DONALD W. BANNER
*Commissioner of Patents and Trademarks*